(12) United States Patent
Barnett et al.

(10) Patent No.: US 9,202,012 B2
(45) Date of Patent: Dec. 1, 2015

(54) VASCULAR ASSESSMENT SYSTEM

(75) Inventors: Noelle Leslie Barnett, Corona del Mar, CA (US); Vitas Jonas Sipelis, San Clemente, CA (US)

(73) Assignee: Covidien LP, Mansfield, MA (US)

( * ) Notice: Subject to any disclaimer, the term of this patent is extended or adjusted under 35 U.S.C. 154(b) by 505 days.

(21) Appl. No.: 13/162,774

(22) Filed: Jun. 17, 2011

(65) Prior Publication Data
US 2012/0324402 A1    Dec. 20, 2012

(51) Int. Cl.
*G06F 3/048* (2013.01)
*G06F 19/00* (2011.01)

(52) U.S. Cl.
CPC .................................. *G06F 19/3481* (2013.01)

(58) Field of Classification Search
USPC ........ 715/840, 821, 841, 708, 781; 703/2, 11; 705/346
See application file for complete search history.

(56) References Cited

U.S. PATENT DOCUMENTS

| | | | |
|---|---|---|---|
| 4,839,822 A * | 6/1989 | Dormond et al. ............... | 706/45 |
| 4,945,476 A | 7/1990 | Bodick et al. | |
| 5,325,293 A | 6/1994 | Dorne | |
| 6,021,404 A | 2/2000 | Moukheibir | |
| 7,853,899 B1 * | 12/2010 | Damaschke et al. .......... | 715/841 |
| 7,887,475 B1 | 2/2011 | Hayman et al. | |
| 8,321,372 B1 * | 11/2012 | Rakshit et al. .................. | 706/62 |
| 8,706,519 B2 * | 4/2014 | Gliklich ............................ | 705/2 |
| 2002/0004729 A1 * | 1/2002 | Zak et al. ............................ | 705/3 |
| 2002/0021828 A1 | 2/2002 | Papier et al. | |
| 2003/0125609 A1 * | 7/2003 | Becker ............................. | 702/19 |
| 2003/0181790 A1 | 9/2003 | David et al. | |
| 2005/0039127 A1 * | 2/2005 | Davis .............................. | 715/708 |
| 2005/0060205 A1 | 3/2005 | Woods et al. | |
| 2006/0004605 A1 | 1/2006 | Donoghue et al. | |
| 2006/0173858 A1 | 8/2006 | Cantlin et al. | |
| 2006/0222596 A1 * | 10/2006 | Askari et al. .................. | 424/9.41 |
| 2006/0235669 A1 * | 10/2006 | Charbel et al. .................. | 703/11 |
| 2007/0094197 A1 * | 4/2007 | Datena et al. .................... | 706/46 |
| 2007/0118164 A1 | 5/2007 | Jung et al. | |
| 2008/0244375 A1 * | 10/2008 | Gentile et al. ................. | 715/205 |
| 2009/0019400 A1 * | 1/2009 | Matsumoto .................... | 715/840 |
| 2009/0070145 A1 * | 3/2009 | Haider .............................. | 705/3 |
| 2009/0083203 A1 * | 3/2009 | Cho et al. ......................... | 706/21 |
| 2009/0094053 A1 | 4/2009 | Jung et al. | |

(Continued)

FOREIGN PATENT DOCUMENTS

| WO | WO-96/19774 A1 | 6/1996 |
|---|---|---|
| WO | WO-03/100542 A2 | 12/2003 |
| WO | WO-2011/006241 A1 | 1/2011 |

*Primary Examiner* — Ryan Pitaro
*Assistant Examiner* — Mahelet Shiberou
(74) *Attorney, Agent, or Firm* — Mark J. Kertz, Esq.

(57) ABSTRACT

Systems and methods for aiding treatment of a medical condition are described. One such method includes: displaying at an interface (i) a graphical representation of at least a portion of an anatomic area, and (ii) regions of interest at locations in the representation, each of the regions representing an anatomic site of a medical event; receiving from a user a first selection representing a first site among the anatomic sites; determining a first set of morphologies of the first site, each member of the first set being clinically associated with occurrence of the event at a diseased portion of the first site; and determining, based on a second selection by the user, a second set of morphologies of the first site, each member of the second set including at least one of a shape and a size of the diseased portion associated with the first member.

13 Claims, 17 Drawing Sheets

(56) References Cited

U.S. PATENT DOCUMENTS

2009/0276246 A1* 11/2009 Haskell et al. ............... 705/3
2009/0288000 A1   11/2009 McPherson
2010/0223295 A1*  9/2010 Stanley et al. ............ 707/794
2010/0318936 A1* 12/2010 Tremblay et al. ......... 715/781
2010/0328235 A1   12/2010 Taute
2011/0004487 A1    1/2011 Schoenberg
2011/0016427 A1*   1/2011 Douen ...................... 715/828
2011/0179389 A1*   7/2011 Douen ...................... 715/843
2012/0047105 A1*   2/2012 Saigal et al. ............... 706/52

* cited by examiner

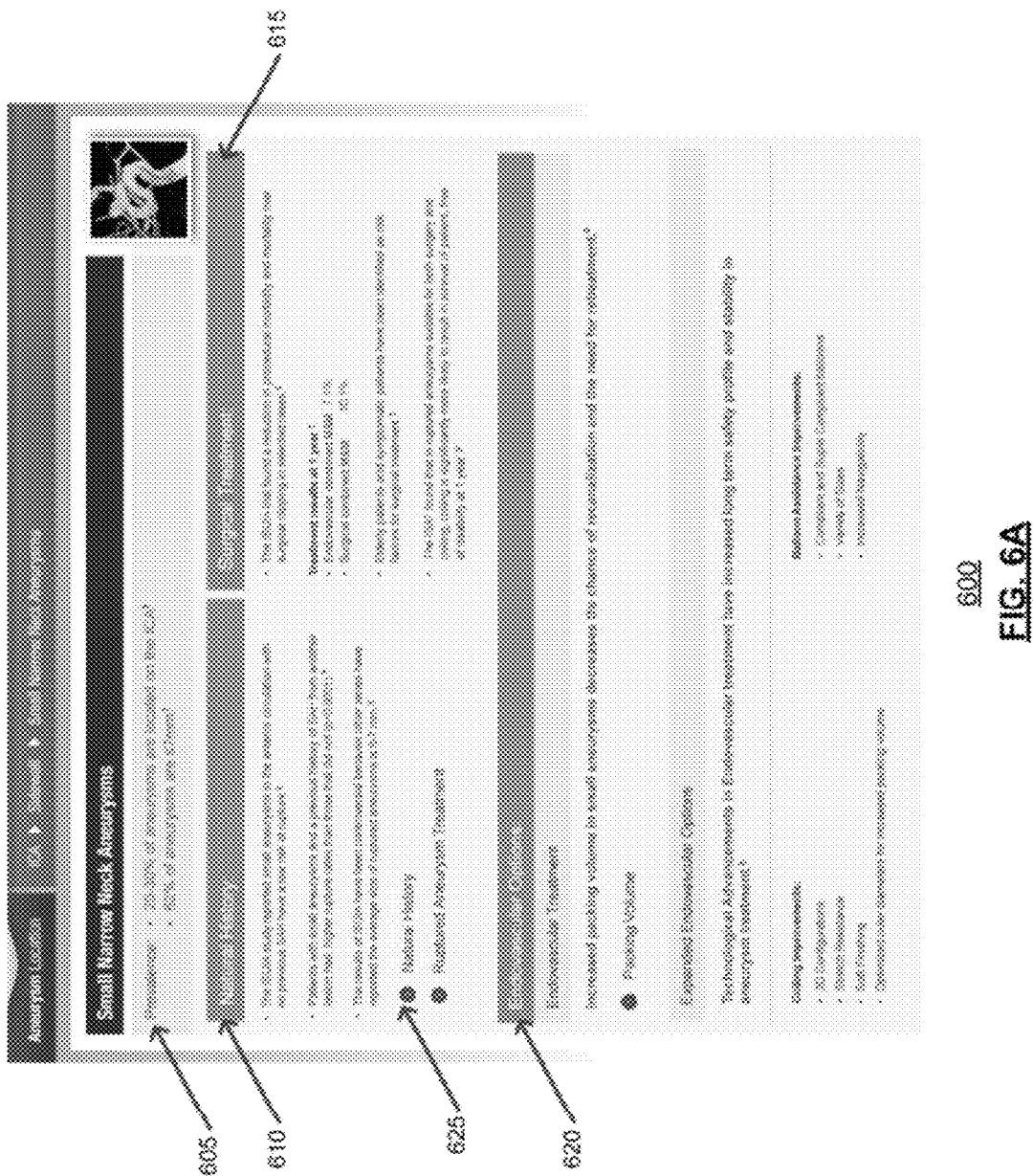

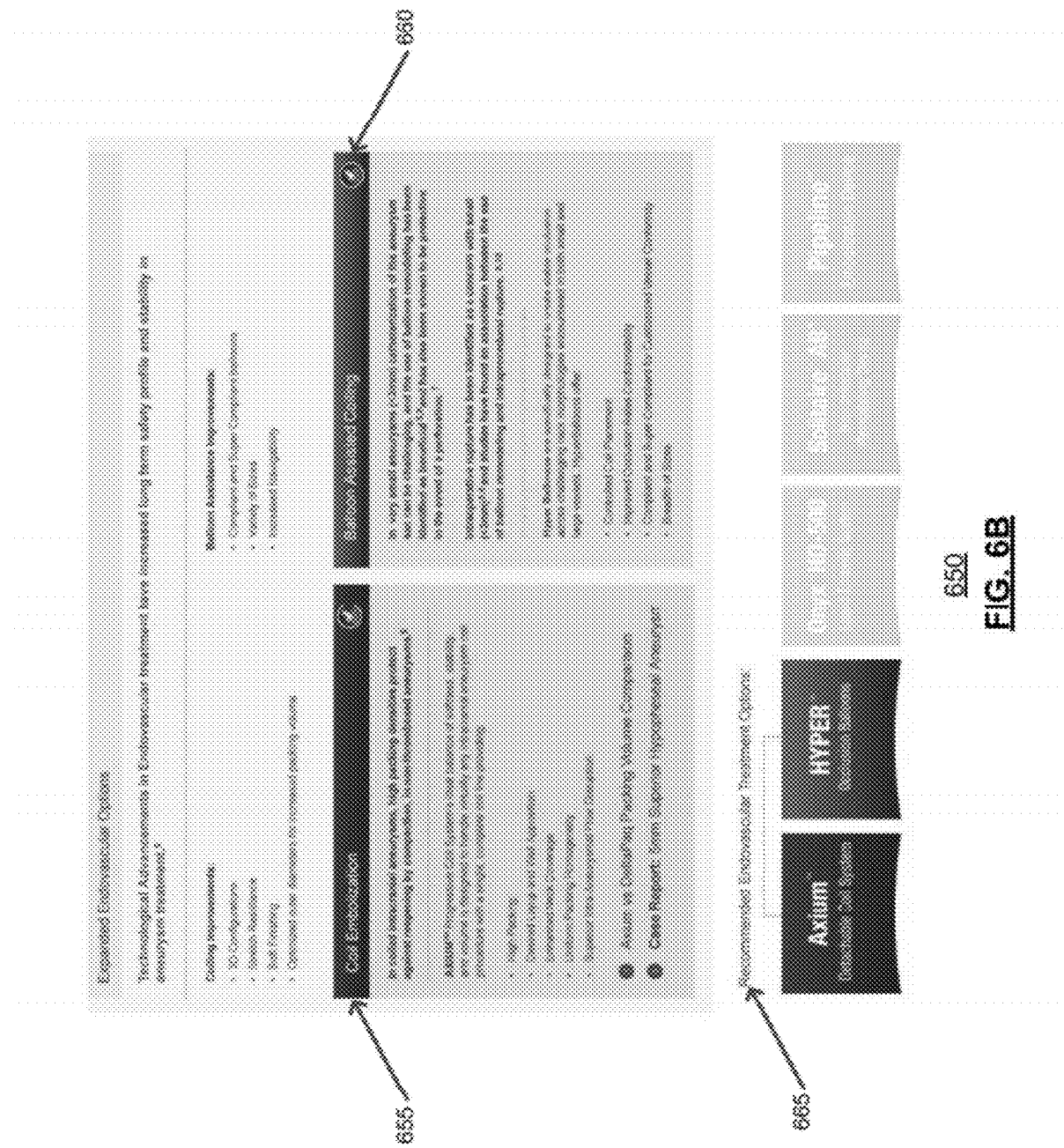

VASCULAR ASSESSMENT SYSTEM

BACKGROUND

The subject technology relates to aiding treatment of a medical condition.

In certain fields of medicine, deciding on a treatment plan for a patient may be very difficult. Some treatment modalities may lack a sufficient body of clinical research that may be relied upon to establish safety and efficacy. Existing clinical evidence may also be difficult to find and analyze. In some fields, a multitude of treatment options may exist along with a confusing array of research and test results for each of the options. The number of options and the sheer amount of research material for each option may make it difficult to identify the best treatment option for a patient.

Moreover, every instance of a medical condition (e.g., a vascular disease) is associated with a particular set of characteristics that may vary from one instance of the condition to another. As a result, some treatment options may be better for one instance of a medical condition with a particular set of characteristics than for another instance with different characteristics. Identifying, updating, and recalling which treatment options are preferred for a particular set of characteristics of a medical condition may be difficult. Furthermore, even if one or more treatment options may be identified, if they involve the use of medical devices or drugs, it may be difficult to determine which of the options is best for use in a given patient.

SUMMARY

The subject technology is illustrated, for example, according to various aspects described below. Various examples of aspects of the subject technology are described as numbered clauses (1, 2, 3, etc.) for convenience. These are provided as examples, and do not limit the subject technology.

1. A method of aiding interventional treatment of a vascular disease, comprising:
    displaying at an interface (i) a graphical representation of at least a portion of a vascular area comprising at least one of an arterial bifurcation and a venous confluence, and (ii) a plurality of regions of interest at locations in the representation, each of the regions representing a distinct anatomic site of an event at the vascular area;
    wherein the event comprises at least one of thrombosis, rupture, and bleeding;
    receiving from a user a first selection, of a first of the regions, the first region representing a first site among the plurality of anatomic sites;
    determining, based on the first selection, a first set of morphologies of the first site, each member of the first set being clinically associated with occurrence of the event at a diseased portion of the first site;
    displaying the members of the first set to the user;
    receiving from the user a second selection, of a first member of the first set;
    determining, based on the second selection, a second set of morphologies of the first site, each member of the second set comprising at least one of a shape and a size of the diseased portion associated with the first member; and
    displaying the members of the second set to the user.

2. The method of clause 1, wherein the diseased portion comprises at least one of an aneurysm and an arteriovenous malformation.

3. The method of clause 1, further comprising:
    receiving from the user a third selection, of a first member of the second set;
    determining, based on the third selection, an item of clinical information to display to the user; and
    displaying the item of clinical information to the user.

4. The method of clause 3, wherein the item of clinical information comprises a selection of at least one therapeutic device type suitable for treating the diseased portion, wherein selection of the at least one therapeutic device type is based on at least one of the first selection and the second selection.

5. The method of clause 3, wherein the item of clinical information includes at least one link to an interface containing information about a particular therapeutic device.

6. The method of clause 5, wherein the information about a particular therapeutic device comprises at least one of device features, device benefits, case reports associated with the device, device configurations, and a summary of studies associated with the device.

7. The method of clause 3, wherein the item of clinical information comprises at least one treatment option associated with the first selection and the second selection.

8. The method of clause 3, wherein the item of clinical information comprises information about a plurality of treatment options including at least one of comparisons between treatment options, outcome statistics of treatment options, and case reports.

9. The method of clause 3, wherein the item of clinical information comprises a selection of information about the event at the vascular area, wherein selection of the information about the event is based on at least one of the first selection and the second selection.

10. A machine-readable medium comprising instructions stored therein, which when executed by a machine, cause the machine to perform operations comprising:
    displaying at an interface (i) a graphical representation of a portion of a mammalian body, and (ii) a plurality of regions of interest at locations in the representation, each of the regions representing a distinct anatomic site of a potential medical event;
    receiving from a user a first selection, of a first of the regions, the first region representing a first site among the plurality of anatomic sites;
    determining, based on the first selection, a first set of morphologies of the first site, each member of the first set being clinically associated with occurrence of the event at a diseased portion of the first site;
    displaying the members of the first set to the user;
    receiving from the user a second selection, of a first member of the first set;
    determining, based on the second selection, a second set of morphologies of the first site, each member of the second set comprising at least one of a shape and a size of the diseased portion associated with the first member; and
    displaying the members of the second set to the user.

11. The machine-readable medium of clause 10, wherein the graphical representation of a portion of the mammalian body comprises a vascular area of the mammalian body.

12. The machine-readable medium of clause 10, wherein the diseased portion comprises at least one of an aneurysm and an arteriovenous malformation.

13. The machine-readable medium of clause 10, further comprising:
    receiving from the user a third selection, of a first member of the second set;

determining, based on the third selection, an item of clinical information to display to the user; and
displaying the item of clinical information to the user.

14. The machine-readable medium of clause 13, wherein the item of clinical information comprises a selection of at least one therapeutic device type suitable for treating the diseased portion, wherein selection of the at least one therapeutic device type is based on at least one of the first selection and the second selection.

15. The machine-readable medium of clause 13, wherein the item of clinical information includes at least one link to an interface containing information about a particular therapeutic device.

16. The machine-readable medium of clause 15, wherein the information about a particular therapeutic device comprises at least one of device features, device benefits, case reports associated with the device, device configurations, and a summary of studies associated with the device.

17. The machine-readable medium of clause 13, wherein the item of clinical information comprises information about a plurality of treatment options including at least one of comparisons between treatment options, outcome statistics of treatment options, and case reports.

18. The machine-readable medium of clause 13, wherein the item of clinical information comprises a selection of information about the event, wherein selection of the information about the event is based on at least one of the first selection and the second selection.

19. A system for aiding interventional treatment of a vascular disease, the system comprising:
an output interface configured to present data;
an input interface configured to receive input data;
a processor; and
a storage device configured to store instructions that, when executed by the processor, cause the processor to:
display, at the output interface, (i) a graphical representation of at least a portion of a vascular area comprising at least one of an arterial bifurcation and a venous confluence, and (ii) a plurality of regions of interest at locations in the representation, each of the regions representing a distinct anatomic site of an event at the vascular area;
wherein the event comprises at least one of thrombosis, rupture, and bleeding;
receive, via the input interface, a first selection, of a first of the regions, the first region representing a first site among the plurality of anatomic sites;
determine, based on the first selection, a first set of morphologies of the first site, each member of the first set being clinically associated with occurrence of the event at a diseased portion of the first site;
display, at the output interface, the members of the first set to the user;
receive, via the input interface, a second selection, of a first member of the first set;
determine, based on the second selection, a second set of morphologies of the first site, each member of the second set comprising at least one of a shape and a size of the diseased portion associated with the first member; and
display, at the output interface, the members of the second set to the user.

20. The system of clause 19, wherein the storage device is further configured to store instructions that, when executed by the processor, cause the processor to:
receive, via the input interface, a third selection, of a first member of the second set;
determine, based on the third selection, an item of clinical information to display to the user; and
display, at the output-interface, the item of clinical information to the user.

21. A method of aiding treatment of a medical condition, comprising:
displaying at an interface (i) a graphical representation of at least a portion of a body, and (ii) a plurality of regions of interest at locations in the representation, each of the regions representing a distinct anatomic site of an event at the body;
receiving from a user a first selection, of a first of the regions, the first region representing a first site among the plurality of anatomic sites;
determining, based on the first selection, a first set of morphologies of the first site, each member of the first set being clinically associated with occurrence of the event at a diseased portion of the first site;
displaying the members of the first set to the user;
receiving from the user a second selection, of a first member of the first set;
determining, based on the second selection, a second set of morphologies of the first site, each member of the second set comprising at least one of a shape and a size of the diseased portion associated with the first member; and
displaying the members of the second set to the user.

22. The method of clause 21, wherein the diseased portion comprises at least one of an aneurysm and an arteriovenous malformation.

23. The method of clause 21, further comprising:
receiving from the user a third selection, of a first member of the second set;
determining, based on the third selection, an item of clinical information to display to the user; and
displaying the item of clinical information to the user.

24. The method of clause 23, wherein the item of clinical information comprises a selection of at least one therapeutic device type suitable for treating the diseased portion, wherein selection of the at least one therapeutic device type is based on at least one of the first selection and the second selection.

25. The method of clause 23, wherein the item of clinical information includes at least one link to an interface containing information about a particular therapeutic device.

26. The method of clause 25, wherein the information about a particular therapeutic device comprises at least one of device features, device benefits, case reports associated with the device, device configurations, and a summary of studies associated with the device.

27. The method of clause 23, wherein the item of clinical information comprises at least one treatment option associated with the first selection and the second selection.

28. The method of clause 23, wherein the item of clinical information comprises information about a plurality of treatment options including at least one of comparisons between treatment options, outcome statistics of treatment options, and case reports.

29. The method of clause 23, wherein the item of clinical information comprises a selection of information about the event at the body, wherein selection of the information about the event is based on at least one of the first selection and the second selection.

30. A machine-readable medium comprising instructions stored therein, which when executed by a machine, cause the machine to perform operations comprising:
displaying at an interface (i) a graphical representation of a portion of a mammalian body, and (ii) a plurality of regions of interest at locations in the representation, each of the regions representing a distinct anatomic site of a potential medical event;

receiving from a user a first selection, of a first of the regions, the first region representing a first site among the plurality of anatomic sites;

determining, based on the first selection, a first set of morphologies of the first site, each member of the first set being clinically associated with occurrence of the event at a diseased portion of the first site;

displaying the members of the first set to the user;

receiving from the user a second selection, of a first member of the first set;

determining, based on the second selection, a second set of morphologies of the first site, each member of the second set comprising at least one of a shape and a size of the diseased portion associated with the first member; and displaying the members of the second set to the user.

31. The machine-readable medium of clause 30, wherein the graphical representation of a portion of the mammalian body comprises a vascular area of the mammalian body.

32. The machine-readable medium of clause 30, wherein the diseased portion comprises at least one of an aneurysm and an arteriovenous malformation.

33. The machine-readable medium of clause 30, further comprising:

receiving from the user a third selection, of a first member of the second set;

determining, based on the third selection, an item of clinical information to display to the user; and displaying the item of clinical information to the user.

34. The machine-readable medium of clause 33, wherein the item of clinical information comprises a selection of at least one therapeutic device type suitable for treating the diseased portion, wherein selection of the at least one therapeutic device type is based on at least one of the first selection and the second selection.

35. The machine-readable medium of clause 33, wherein the item of clinical information includes at least one link to an interface containing information about a particular therapeutic device.

36. The machine-readable medium of clause 35, wherein the information about a particular therapeutic device comprises at least one of device features, device benefits, case reports associated with the device, device configurations, and a summary of studies associated with the device.

37. The machine-readable medium of clause 33, wherein the item of clinical information comprises information about a plurality of treatment options including at least one of comparisons between treatment options, outcome statistics of treatment options, and case reports.

38. The machine-readable medium of clause 33, wherein the item of clinical information comprises a selection of information about the event, wherein selection of the information about the event is based on at least one of the first selection and the second selection.

39. A system for aiding treatment of a medical condition, the system comprising:

an output interface configured to present data;
an input interface configured to receive input data;
a processor; and
a storage device configured to store instructions that, when executed by the processor, cause the processor to:
display, at the output interface, (i) a graphical representation of at least a portion of a body, and (ii) a plurality of regions of interest at locations in the representation, each of the regions representing a distinct anatomic site of an event at the body;

receive, via the input interface, a first selection, of a first of the regions, the first region representing a first site among the plurality of anatomic sites;

determine, based on the first selection, a first set of morphologies of the first site, each member of the first set being clinically associated with occurrence of the event at a diseased portion of the first site;

display, at the output interface, the members of the first set to the user; receive, via the input interface, a second selection, of a first member of the first set;

determine, based on the second selection, a second set of morphologies of the first site, each member of the second set comprising at least one of a shape and a size of the diseased portion associated with the first member; and display, at the output interface, the members of the second set to the user.

40. The system of clause 39, wherein the storage device is further configured to store instructions that, when executed by the processor, cause the processor to:

receive, via the input interface, a third selection, of a first member of the second set;

determine, based on the third selection, an item of clinical information to display to the user; and display, at the output-interface, the item of clinical information to the user.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate disclosed aspects of the subject technology and together with the description serve to explain the principles of the subject technology.

FIG. 6A is a portion of a graphical interface that displays items of clinical information, in accordance with some aspects of the subject technology.

FIG. 6B is a portion of a graphical interface that displays items of clinical information, in accordance with some aspects of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

In accordance with various aspects of the subject technology, systems and methods for aiding treatment of a vascular disease are disclosed. Such a system may guide users (e.g., doctors, nurses, other medical practitioners, patients, etc.) to various treatment options for a particular medical diagnosis or diagnosed condition in a patient by providing an interface that may be used to quickly and efficiently identify certain characteristics or morphologies associated with the patient's medical condition, determining appropriate treatment options based on the identified characteristics of the patient's medical condition, and presenting information about the treatment options to users. The presented information may aid the user in making an informed decision on how to treat the patient's medical condition. The presented information may also help educate users (e.g., patients or friend and family of a patient) about the potential treatment options for the patient's diagnosed medical condition.

Figure 1:
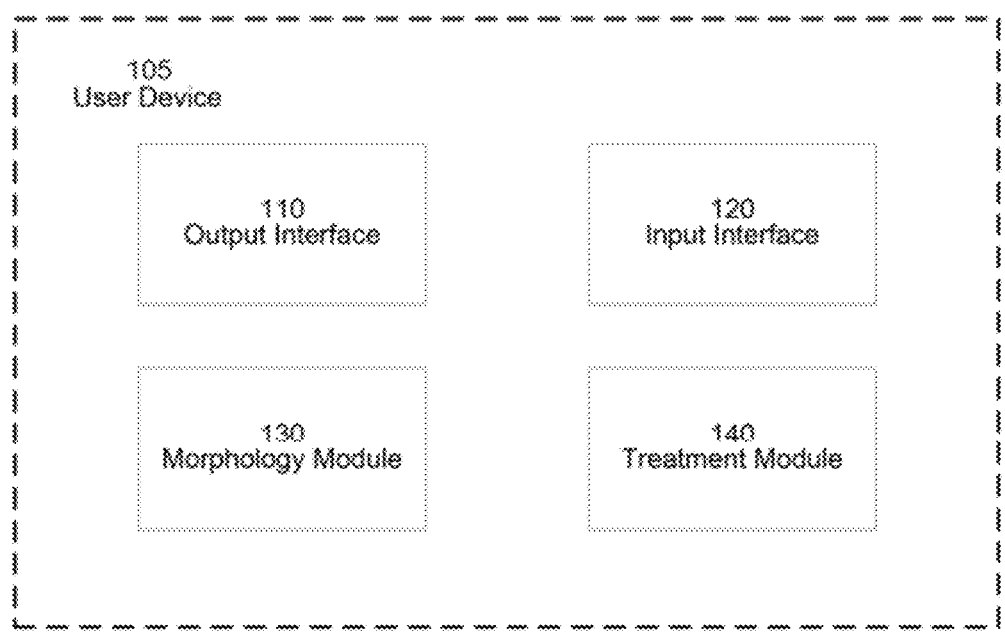
FIG. 1 is a conceptual block diagram illustrating an environment 100 for aiding treatment of a medical condition, in accordance with various aspects of the subject technology.

FIG. 1 is a conceptual block diagram illustrating an environment 100 for aiding treatment of a medical condition, in accordance with various aspects of the subject technology. Although FIG. 1 illustrates a single system environment 100, other aspects of the subject technology may include other configurations including, for example, client-server networked environments or peer-to-peer environments.

The environment 100 may include at least one user device 105 with an input interface (e.g., a touch-screen, a mouse, a keyboard, a stylus interface, a voice recognition unit, etc.), an output interface (e.g., a monitor, a speaker, etc.), and processing capabilities. For example, user device 105 may be a computer, a laptop, a mobile device (e.g., a phone, tablet, personal digital assistant (PDA)), or any other machine with a processor, memory, and input/output capabilities.

In some aspects, the user device 105 may include an output interface 110, an input interface 120, a morphology module 130, and a treatment module 140. The modules illustrated in FIG. 1 may include software instructions encoded in a medium and executed by a processor, computer hardware components, or a combination of both. For example, the modules may each include one or more processors or memories that are used to perform the functions described below. According to some aspects, the various interfaces and modules may share one or more processors or memories.

The interfaces and modules of FIG. 1 may work in combination to help a user identify the particular set of characteristics of a patient's known medical condition and one or more treatment options that fit those set of characteristics of the patient's medical condition. For example, the client device 105 may be used to identify a region of interest that represents a distinct anatomic site in the patient's body where an event or medical condition occurred. Based on where in the patient's body the event or medical condition occurred, the client device 105 may present a set of morphologies to the user to enable the user to further characterize the patient's medical event or condition.

After the user specifies a characteristic of the patient's medical event or condition by selecting one morphology out of the set of morphologies, the client device 105 may generate further sets of morphologies based on the characteristics already specified by the user in order to further identify characteristics of the patient's medical condition and eventually present the user with a number of treatment options directed to the patient's medical diagnoses and information about the treatment options.

In the aspect illustrated by FIG. 1, the output interface 110 may be configured to present users with information via an output device (e.g., a monitor or a speaker). For example, the output interface 110 may generate display information to be displayed on a monitor. The display information may include an interface containing a graphical representation of a body or a portion of a body as well as interaction items (e.g., buttons, links, etc.) that may enable interaction with a user. Some of the interaction items displayed on a monitor may enable a user to navigate an application and select particular characteristics, morphologies, or information about treatment options associated with a known medical condition of a patient.

The input interface 120 may be configured to detect user interactions with the user device 105. For example, the input interface 120 may receive user selections of interaction items via an input device (e.g., a touch screen, a mouse, a keyboard, a microphone, etc.). The selections may include, for example, areas of interest, morphologies, types of medical conditions, types of medical events, treatment options, therapeutic devices, or clinical information.

The morphology module 130 may be configured to determine a set of morphologies to be presented the user, based on one or more user selections received by the input interface 120, to enable the user to specify characteristics of the patient's medical condition. The treatment module 140 may be configured to present the user with treatment options directed to the patient's medical diagnoses along with information that may be helpful in determining course of action or treatment plan. This information may include particular therapeutic devices, device features and benefits, case reports, charts and statistics comparing the treatment options, success rates, etc.

Figure 2:
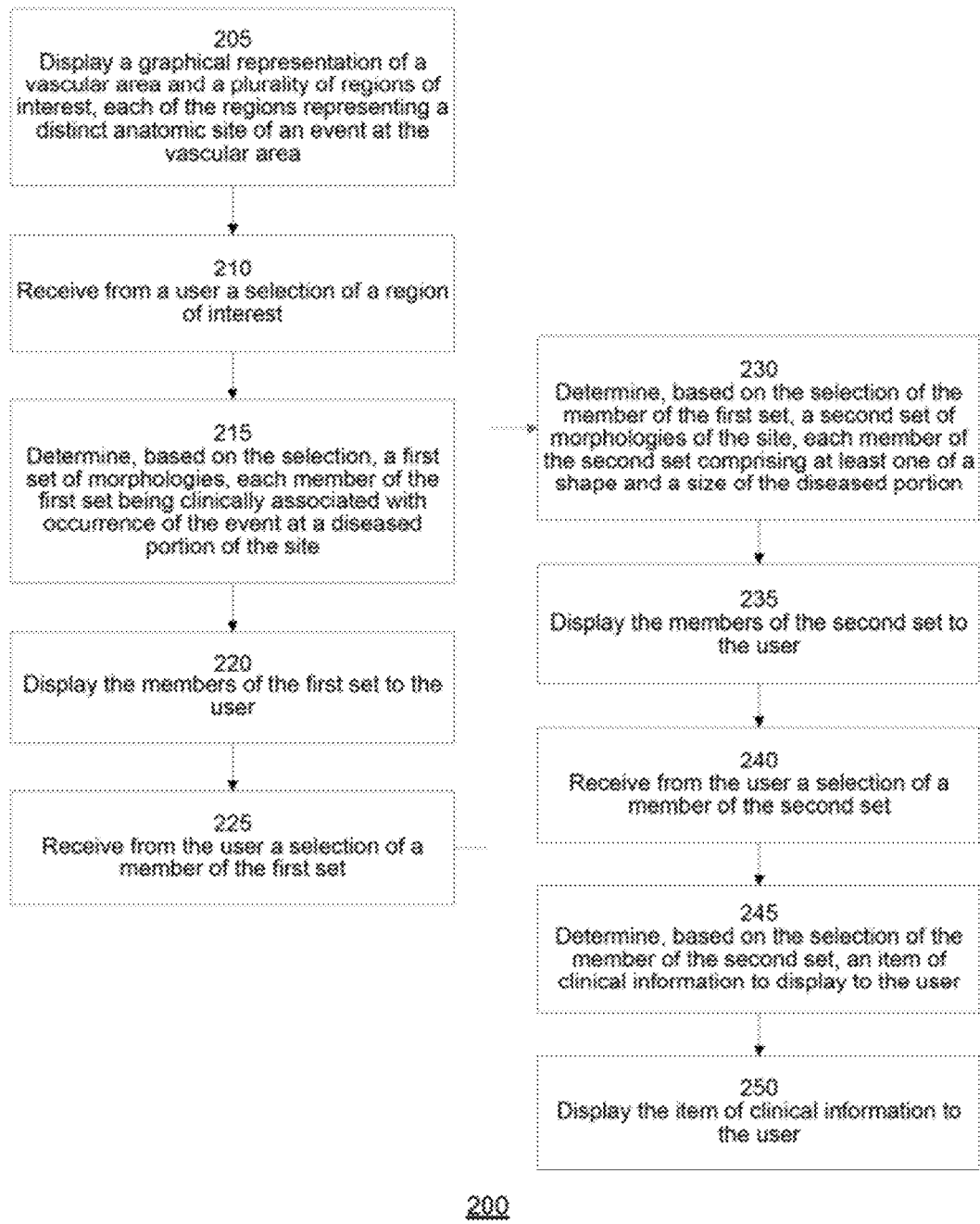
FIG. 2 is a flow chart illustrating a process for aiding treatment of a vascular disease are disclosed, in accordance with various aspects of the subject technology.

The systems, methods, and concepts disclosed may be further illustrated using particular aspects of the subject technology. For example FIG. 2 illustrates a process for aiding treatment of a vascular disease according to various aspects, while FIG. 3-FIG. 8 illustrate particular graphical interfaces for aiding treatment of aneurysms according to various aspects.

As mentioned above, FIG. 2 is a flow chart illustrating a process 200 for aiding treatment of a vascular disease, in accordance with various aspects of the subject technology. Although the process 200 may be used to treat any type of vascular disease at any location in an organism with a vascular system, the operations in FIG. 2 will be discussed with references to the graphical interfaces illustrated in FIG. 3-FIG. 8 in the interest of clarity. Furthermore, it is understood that the subject technology may be used to aid treatment of other types of diseases besides vascular diseases, such as pulmonary, renal, cardiac, musculoskeletal, neurological, dermatological, and gastrointestinal diseases, and others.

Process 200 may begin at operation 205 where an output interface 110 displays a graphical representation of a vascular area and a plurality of regions of interest where each region of interest represents a distinct anatomic site of a medical event at the vascular area. For example, the medical event may include a thrombosis, a rupture, or bleeding. The vascular area displayed in the graphical representation may include, for example, areas with arterial bifurcations and venous confluences.

Figure 3:
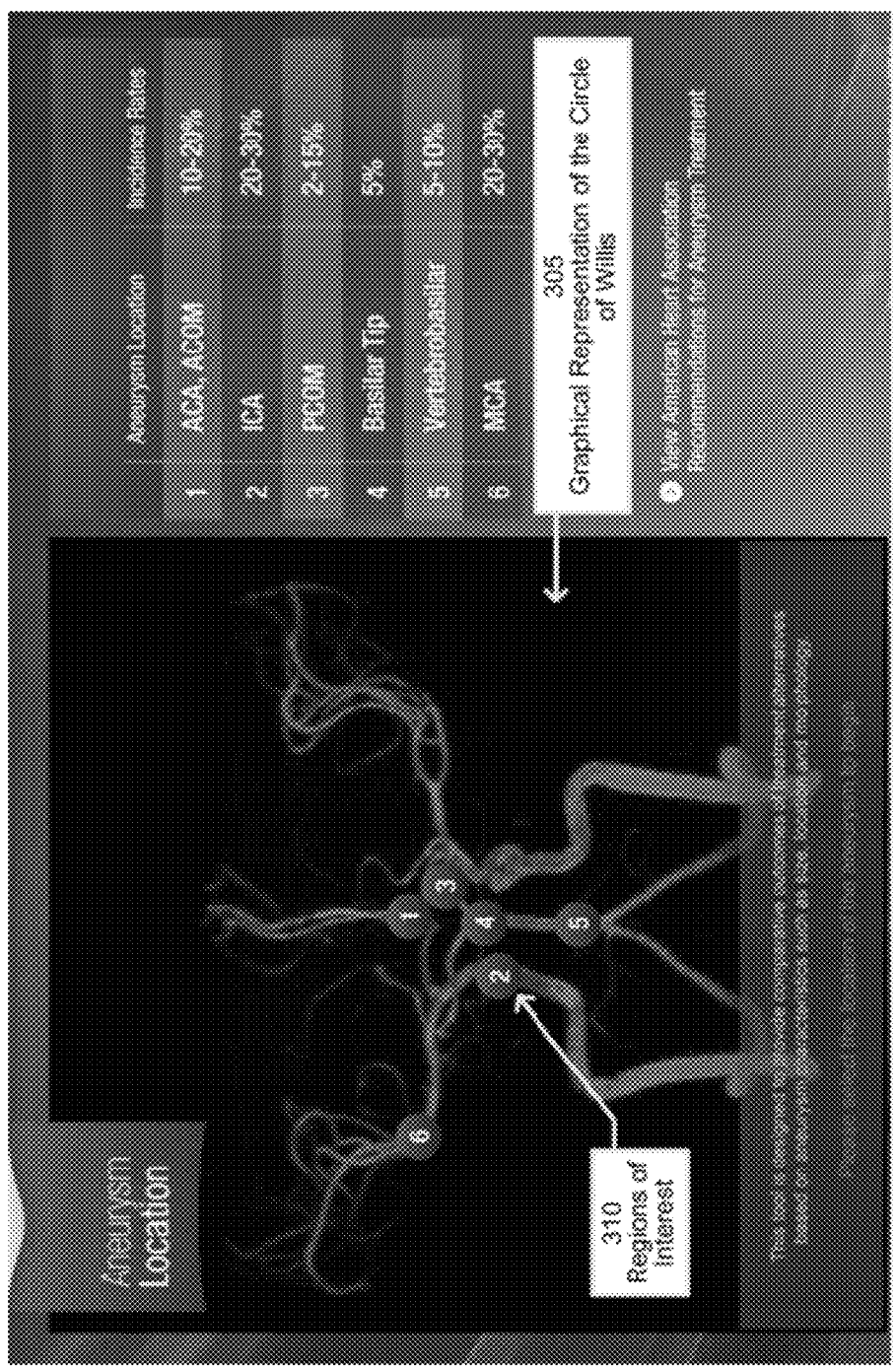
FIG. 3 is a graphical interface that displays a graphical representation of a vascular area, in accordance with some aspects of the subject technology.

FIG. 3 is a graphical interface 300 that displays a graphical representation 305 of a vascular area, in accordance with some aspects of the subject technology. In particular, the graphical representation in FIG. 3 is a graphical representation of the Circle of Willis 305 that may include anterior cerebral arteries, an anterior communicating artery, internal carotid arteries, posterior cerebral arteries, posterior communicating arteries, etc. The graphical interface 300 also includes a number of regions of interest 310 (numbered 1-6) at locations on the graphical representation of the Circle of Willis 305.

Each region of interest 310 represents a distinct anatomic site of an event at the vascular area (e.g., the Circle of Willis). For example, anatomic sites for aneurysms at the Circle of Willis may include the anterior communicating artery (ACA or ACOM), the internal carotid artery (ICA), the posterior communicating artery (PCOM), the basilar tip, the vertebrobasilar area, and the middle cerebral artery (MCA). In some aspects, additional information such as a description of the regions of interest 310 and information about the regions of interest (e.g., incidence rates) may also be shown on the graphical interface 300.

The regions of interest 310 on the display may be interactive and may allow users to select one of the regions of interest. For example, at operation 210, the input interface 120 may receive a user selection of the region of interest 310 identified by the number 2 and referring to the internal carotid artery (ICA) at the Circle of Willis.

Based on the selection of the region of interest 310, at operation 215, the morphology module 130 may determine a first set of morphologies that are clinically associated with the medical event at a diseased portion of the site (e.g., an aneurysm or an arteriovenous malformation at the ICA of the Circle of Willis). The set of morphologies may define one or more characteristics or attributes (e.g., size, shape, color, texture, density, orientation, specific location, etc.) of the medical event at the diseased portion of the site.

Figure 4:
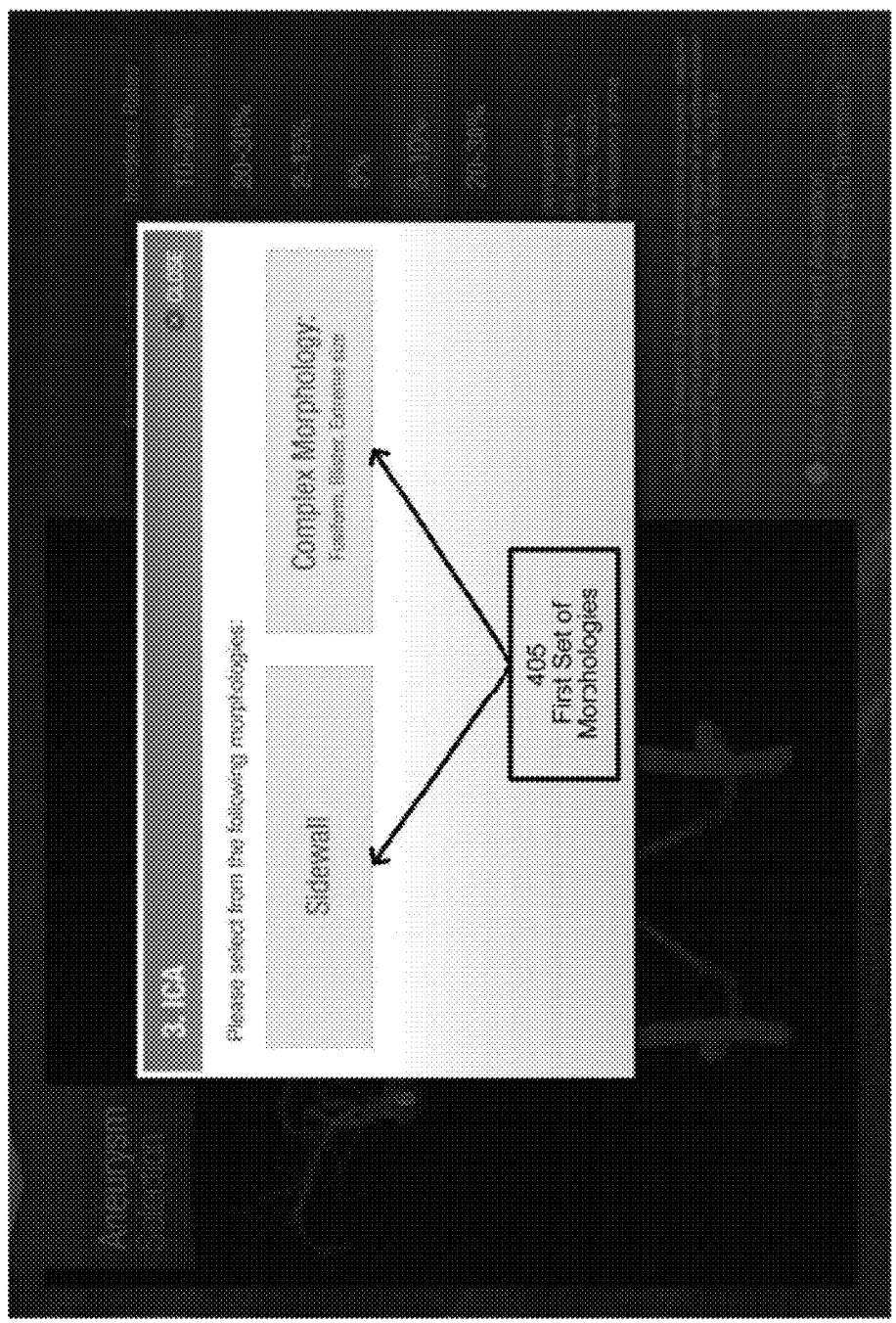
FIG. 4 is a graphical interface that displays a first set of morphologies, in accordance with some aspects of the subject technology.

Once determined, the first set of morphologies may be displayed via the output interface 110 to the user at operation 220. FIG. 4 is a graphical interface 400 that displays a first set of morphologies 405, in accordance with some aspects of the subject technology. The morphologies may include, among other things, a specific aneurysm location at the ICA of the Circle of Willis (e.g., the sidewall) or a type (e.g., a complex morphology). One of the displayed morphologies may be selected by a user and, at operation 225, the input interface 120 may receive a selection of one of the morphologies in the first set.

At operation 230, the morphology module 130 may determine a second set of morphologies based on the user selection of one of the first set of morphologies. The second set of morphologies may include a size or shape of the diseased portion of the site associated with the selected morphology of the first set. The second set of morphologies may also be displayed on the graphical interface at operation 235.

Figure 5:
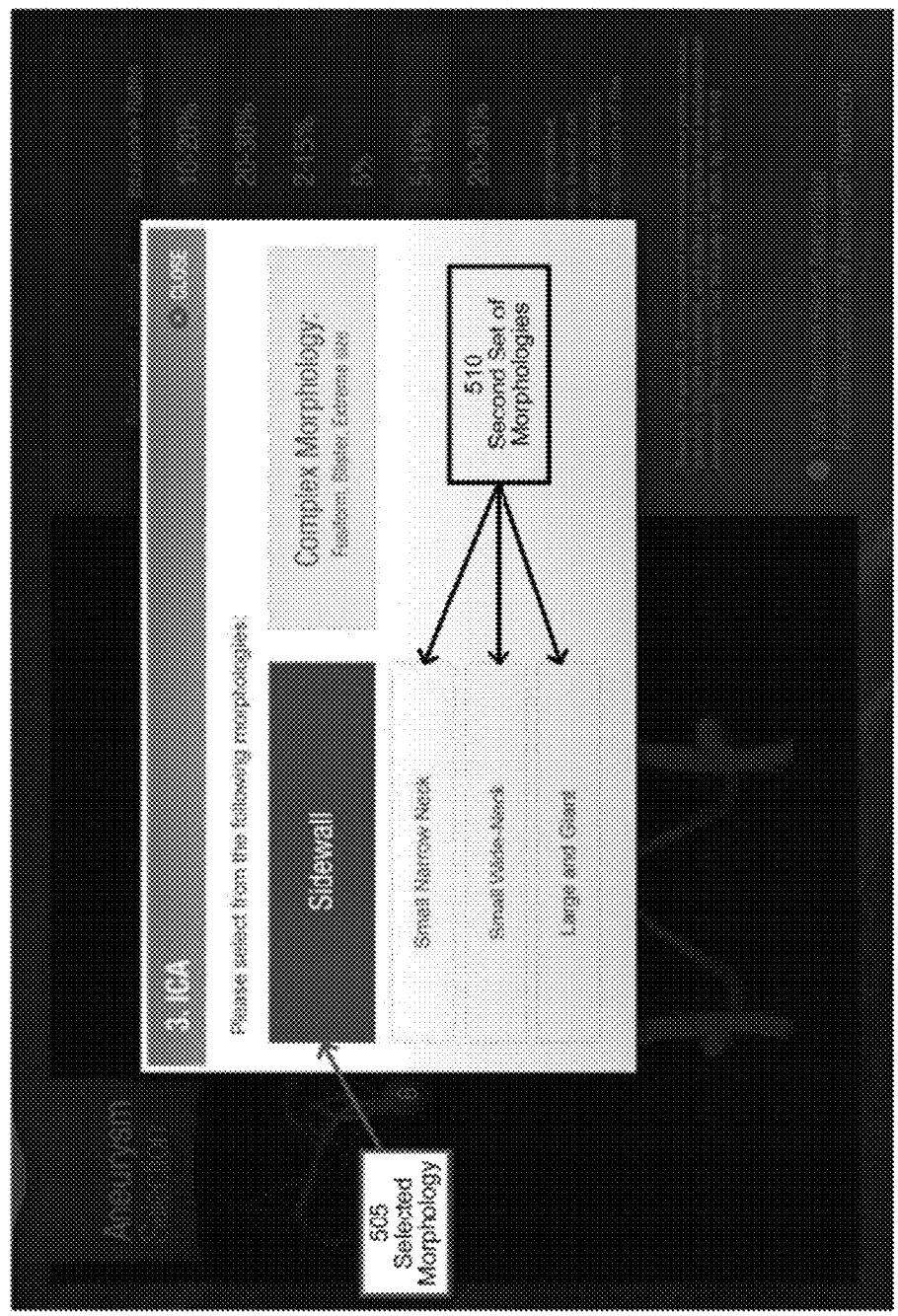
FIG. 5 is a graphical interface that displays a second set of morphologies, in accordance with some aspects of the subject technology.

For example, FIG. 5 is a graphical interface 500 that displays a second set of morphologies 510, in accordance with some aspects of the subject technology. In the illustrated aspect, the user may have selected the "Sidewall" morphology 505 in the first set of morphologies. Based on the selected morphology 505, a second set of morphologies may be generated and displayed. The second set of morphologies 510 may include a "Small Narrow Neck," a "Small Wide-Neck," and a "Large and Giant" morphologies that indicate characteristics of aneurysms on a sidewall of the ICA.

At operation 240, one of the second set of morphologies displayed to a user may be selected by a user and received by the interface module 120. The received user selection may be used by the treatment module 140 to determine, at operation 245, one or more items of clinical information that may be helpful to the user in determining a treatment plan for the patient. The items of clinical information may then be displayed to the user at operation 250 in, for example, a graphical interface (e.g., a landing page or display). The items of clinical information may also be determined based on the various selections made by the user. As such, the clinical information may be directed to the specific location and characteristics of the patient's diagnosed medical condition.

The items of clinical information may be any piece of information that may help a user decide a treatment plan for a patient's diagnosed vascular disease. For example, the item of clinical information may include treatment options, comparisons between treatment options, statistics and charts on the various treatment options, case reports, and studies. The clinical information may also include information about therapeutic devices suitable to treat the patient's medical condition (e.g., device features, benefits, case reports for the device, device configurations, studies, etc.) or links to other information related the patient's medical condition. In some aspects, links or other interface items may be used by a user to access further topics on a number of additional topics such as the natural history of a medical condition, surgical or endovascular treatment options for the medical condition, or information about treatment of particular categories of the medical condition (e.g., ruptured aneurysms).

FIG. 6A is a portion of a graphical interface 600 that displays items of clinical information, in accordance with some aspects of the subject technology. The graphical interface 600 may be displayed to the user in response to various user selections. For example, graphical interface 600 may be displayed in response to the user selecting the "Small Narrow Neck" morphology displayed in the graphical interface 500 in FIG. 5. Graphical interface 600 displays a number of items of clinical information related to small, narrow neck aneurysms located on a sidewall of the ICA.

Graphical interface 600 includes information about the small, narrow neck aneurysms located on the sidewall of the ICA such as prevalence information 605, information about the natural history of small, narrow neck aneurysms 610, information about surgical treatment options 615, and information about endovascular treatment options 620. The information may include a summary of research, studies, or trials, information about new advancements in treatment options, statistics, charts, or other visual aids. Links to additional information (e.g., a link to more information about the natural history 625 of small, narrow neck aneurysms, a link to more information on ruptured aneurysm treatment, a link to more surgical treatment options, or a link to expanded endovascular treatment options) may also be provided.

The items of clinical information may also include treatment options information that is associated with specific therapeutic devices or product lines that may be used. For example, FIG. 6B is a portion of a graphical interface 650 that displays items of clinical information, in accordance with some aspects of the subject technology. In some aspects, the portion of the graphical interface 650 may appear right below the portion of the graphical interface 600 illustrated in FIG. 6A. The bottom portion of the graphical interface 650 may include further information about coil embolization 655 that is associated with a particular device or product (e.g., the Axium detatchable coil system) and information about balloon assisted coiling 660 that is also associated with a particular device or product (e.g., Hyper balloons). The graphical interface 650 may also include recommended treatment options 665 and links to a more information about recommended products associated with the treatment options (e.g., the Axium detachable coil system and the Hyper occlusion balloons). The links may lead to additional graphical interfaces with more detailed information on each of the treatment options and associated therapeutic products.

Figure 6C:
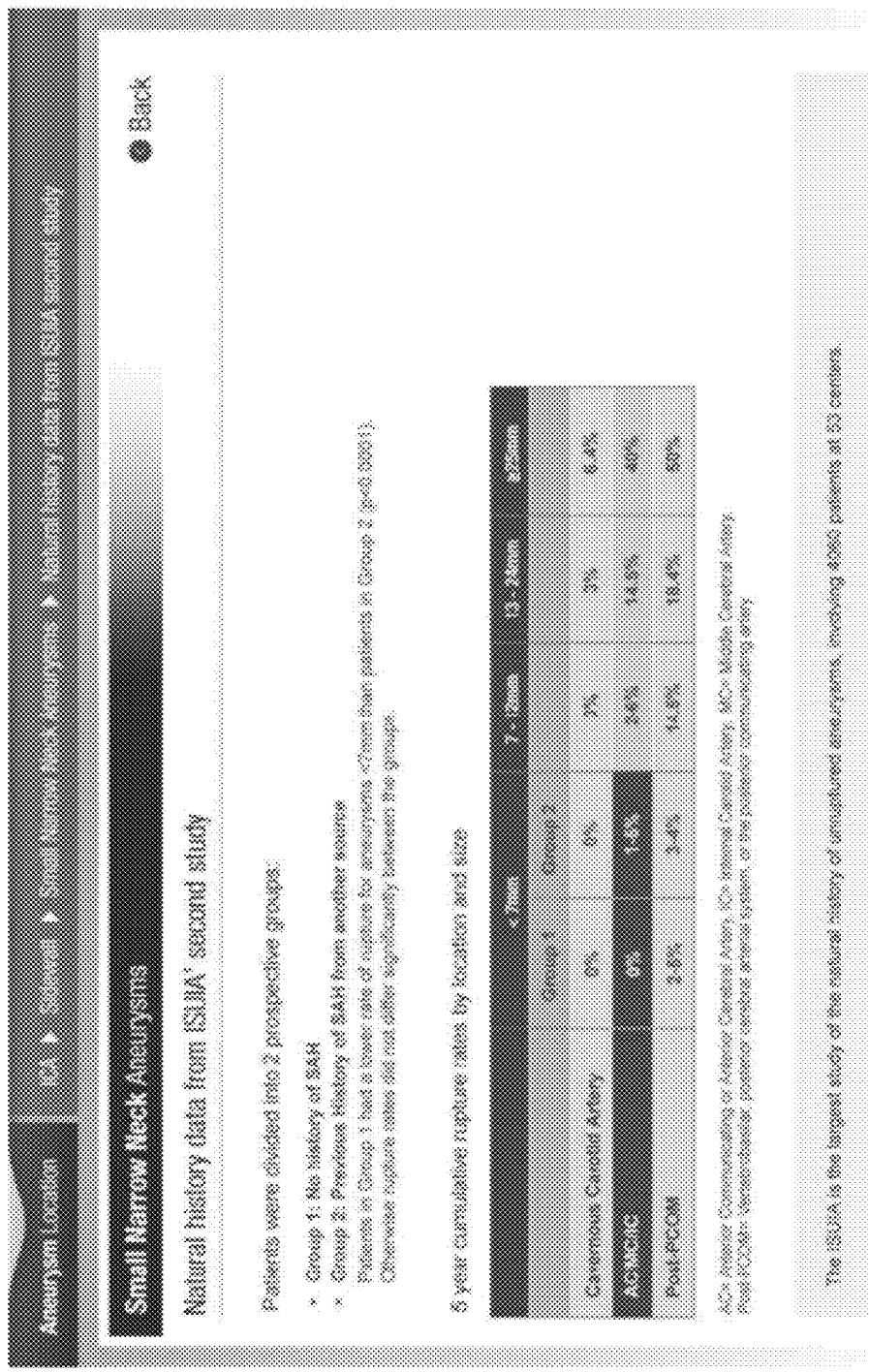
FIG. 6C is a graphical interface that displays items of clinical information, in accordance with some aspects of the subject technology.

FIG. 6C is a graphical interface 680 that displays items of clinical information, in accordance with some aspects of the subject technology. More specifically, FIG. 6C illustrates a natural history of small, narrow neck aneurysms that may be reached by the user selecting the natural history link 625 displayed in graphical interface 600 of FIG. 6A. In some aspects, the natural histories of medical conditions may be a summary of one or more studies and include visual aids (e.g., charts, tables, images, graphs, etc.) to help a user digest the information.

Figure 7A:
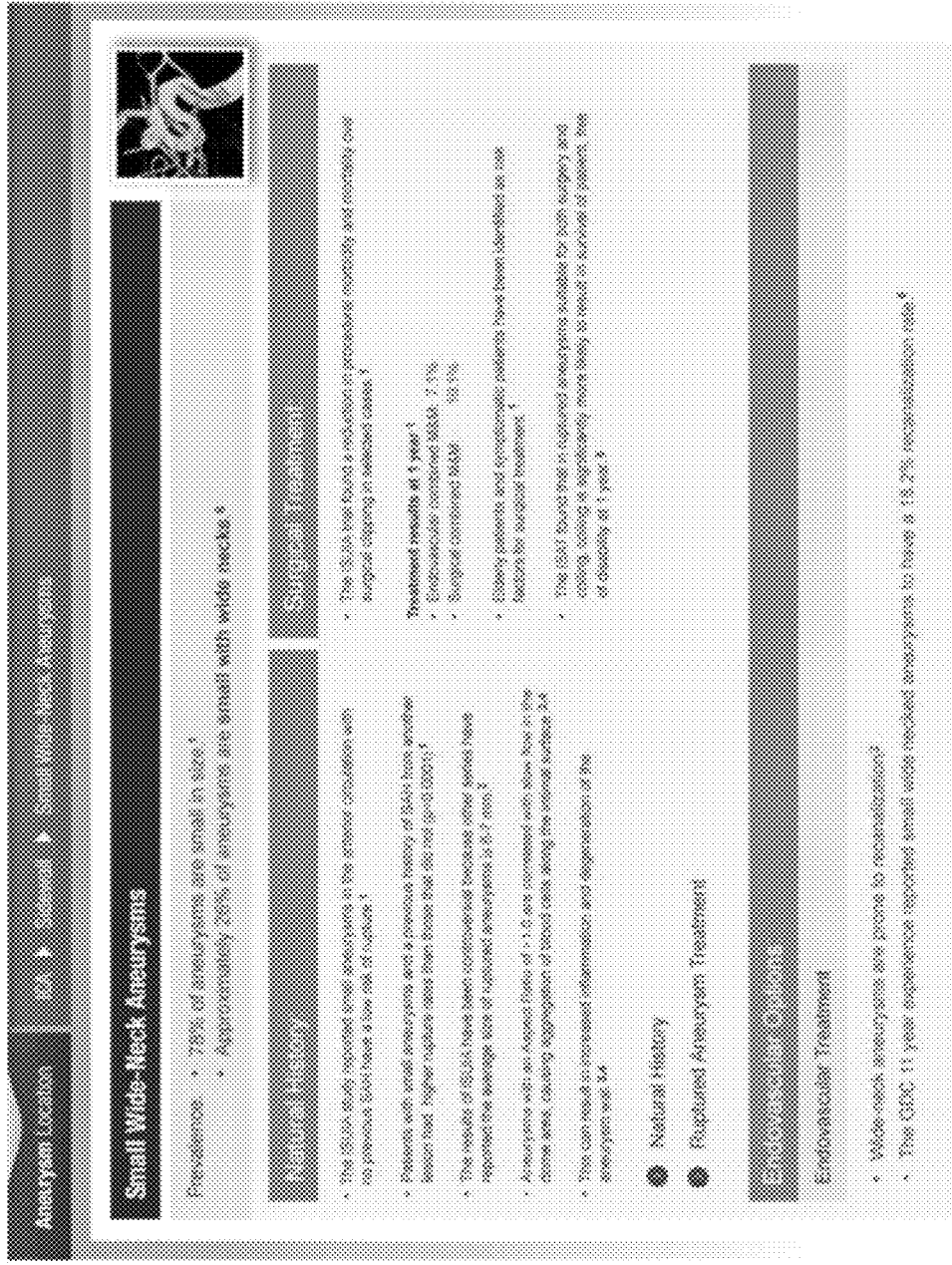
FIG. 7A is a portion of a graphical interface that displays items of clinical information, in accordance with some aspects of the subject technology.

FIG. 7A is a portion of a graphical interface 700 that displays items of clinical information, in accordance with some aspects of the subject technology. The graphical interface 700 may be displayed in response to the user selecting the "Small Wide-Neck" morphology displayed in the graphical interface 500 in FIG. 5. Graphical interface 700 includes information about the small, wide-neck aneurysms located on the sidewall of the ICA such as prevalence information, information about the natural history of small, wide-neck aneurysms, information about surgical treatment options, and information about endovascular treatment options. As will be illustrated with reference to FIG. 7B, a graphical interface may also display case reports, comparative outcomes, and studies that help a user decide a treatment plan.

Figure 7B:
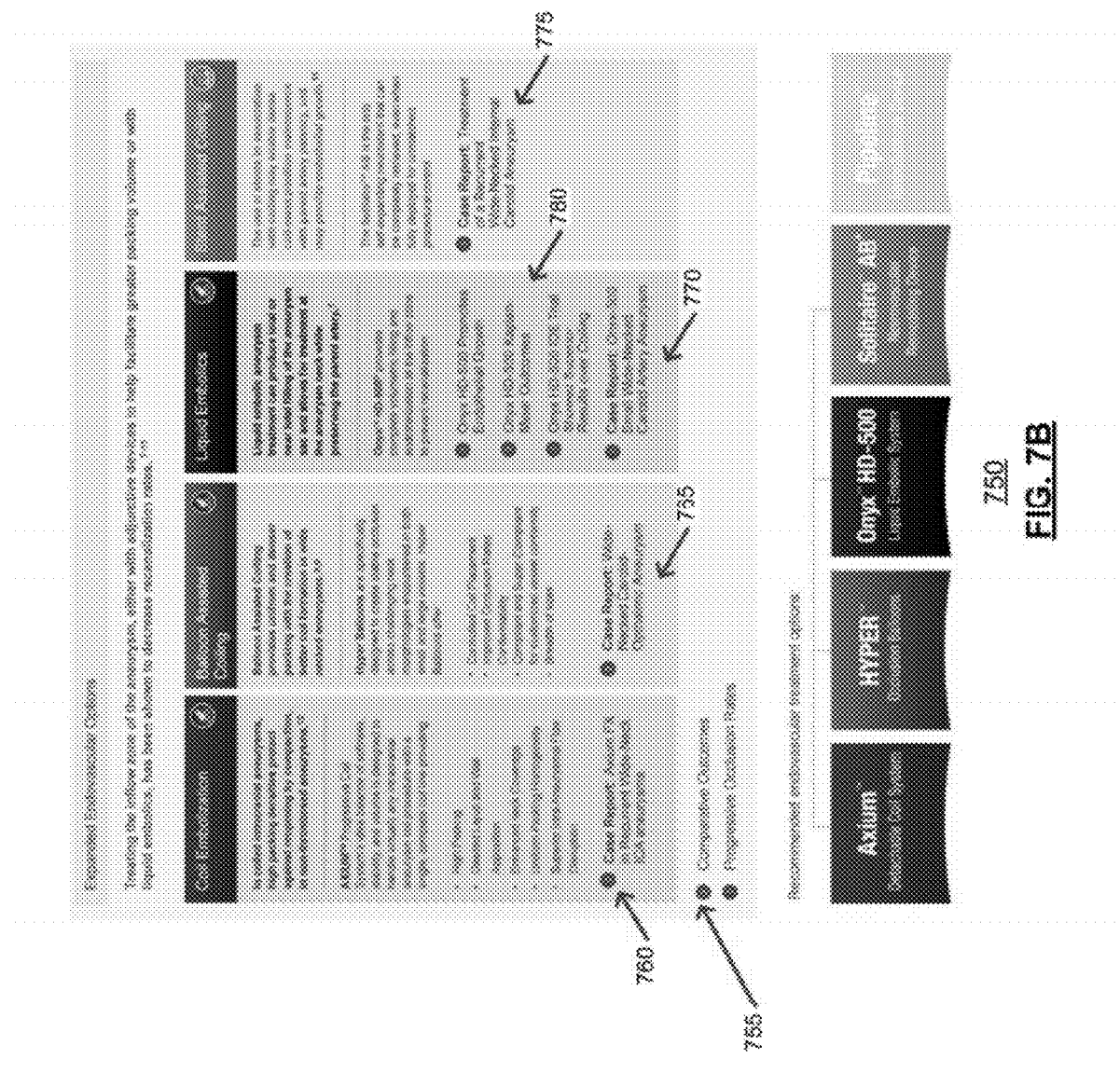
FIG. 7B is a portion of a graphical interface that displays items of clinical information, in accordance with some aspects of the subject technology.

FIG. 7B is a portion of a graphical interface 750 that displays items of clinical information, in accordance with some aspects of the subject technology. In some aspects, the portion of the graphical interface 750 may appear right below the portion of the graphical interface 700 illustrated in FIG. 7A. In addition to displaying information about treatment options and devices or product lines associated with the treatment options, the portion of the graphical interface 750 may also show links to various information comparing the recommended treatment options. For example, there may be links to comparative outcomes of the treatment options 755, links to case reports for one or more of the treatment options (e.g., 760, 765, 770, 775) that may be associated with a therapeutic product for that treatment option, and links to trial results (780).

Figure 8A:
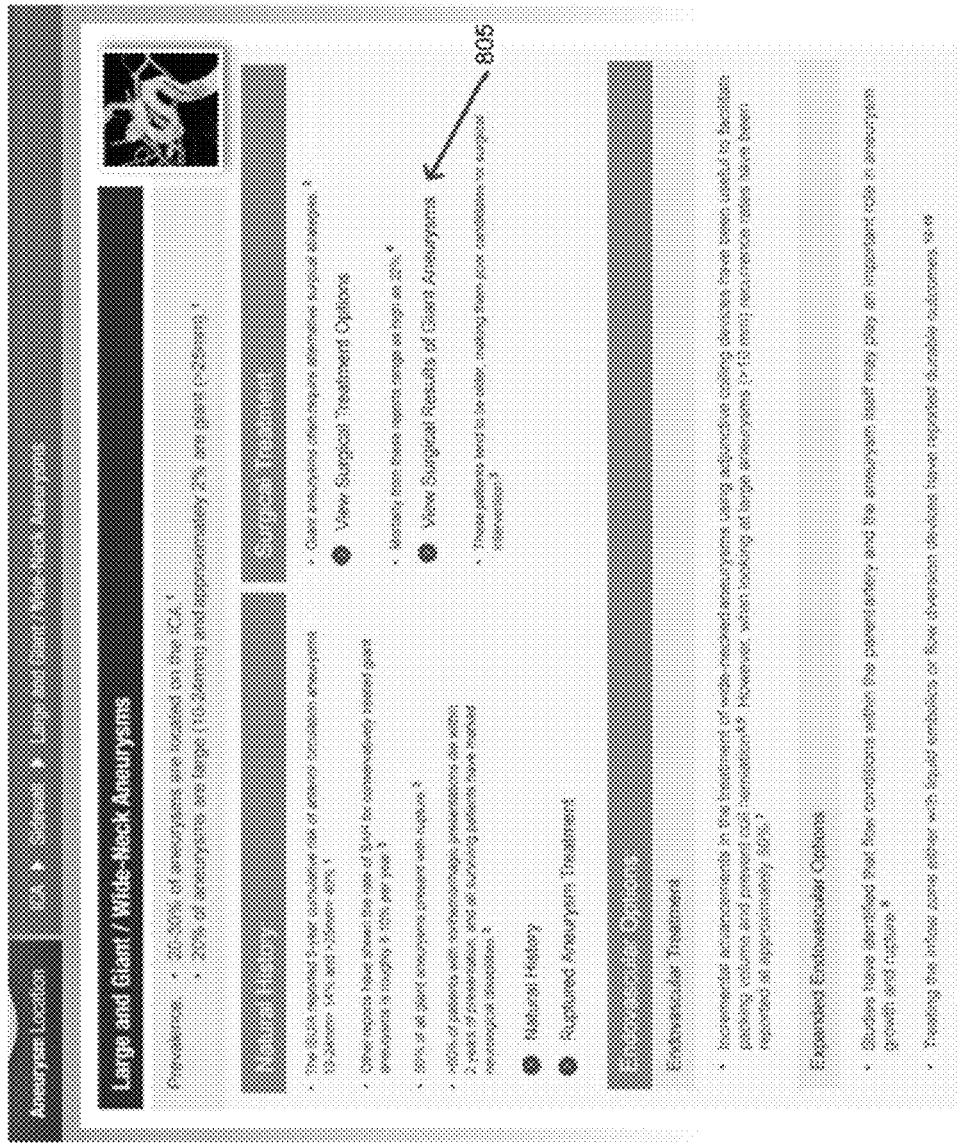
FIG. 8A is a portion of a graphical interface that displays items of clinical information, in accordance with some aspects of the subject technology.

FIG. 8A is a portion of a graphical interface 800 that displays items of clinical information, in accordance with some aspects of the subject technology. The graphical interface 800 may be displayed in response to the user selecting the "Large and Giant" morphology displayed in the graphical interface 500 in FIG. 5. Graphical interface 800 includes information about large and giant or wide-neck aneurysms located on the sidewall of the ICA such as prevalence information, information about the natural history of small, wide-neck aneurysms, information about surgical treatment options, and information about endovascular treatment options. The graphical interface 800 may also include links to information about surgical results 805 so that users may be able to get a better understanding of the surgical options.

Figure 8B:
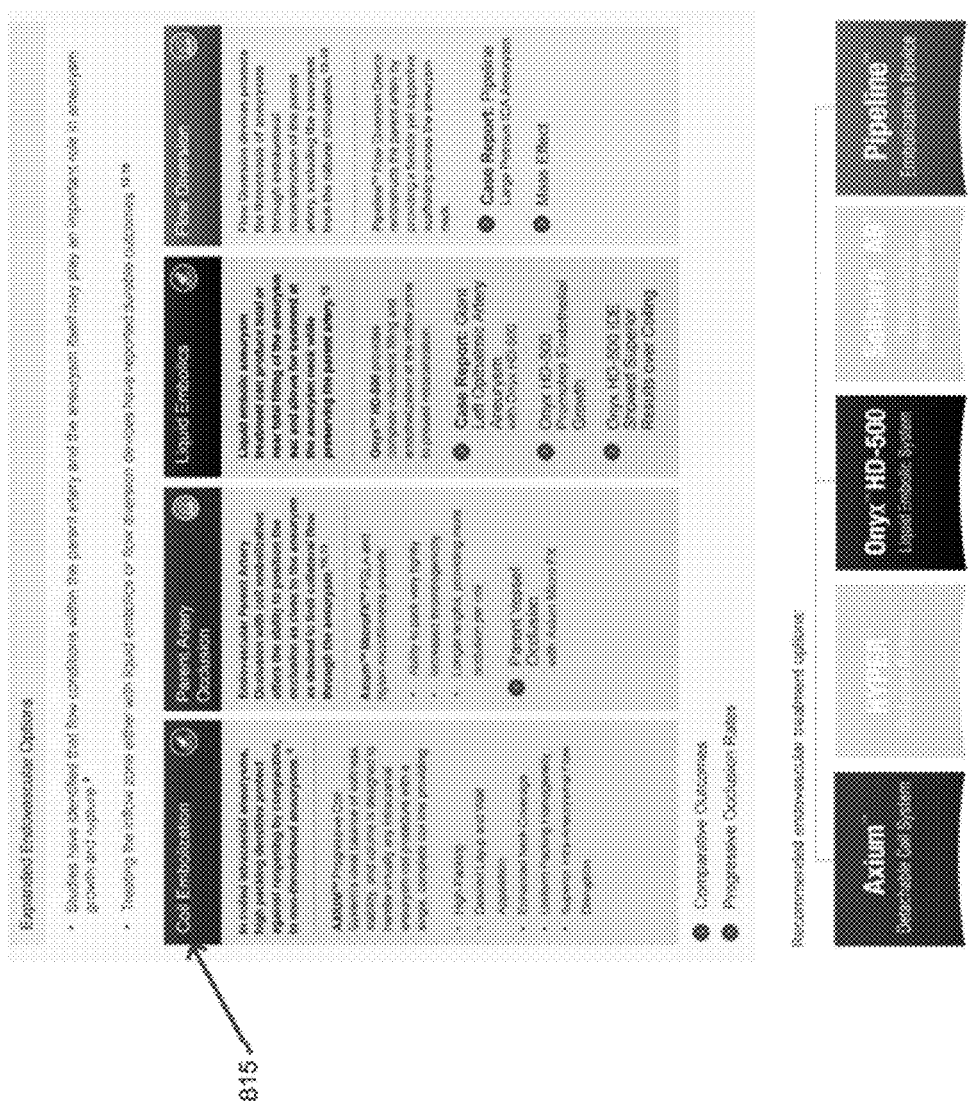
FIG. 8B is a portion of a graphical interface that displays items of clinical information, in accordance with some aspects of the subject technology.

FIG. 8B is a portion of a graphical interface 850 that displays items of clinical information, in accordance with some aspects of the subject technology. In some aspects, the portion of the graphical interface 850 may appear right below the portion of the graphical interface 800 illustrated in FIG. 8A. Graphical interface 850 may display a side-by-side comparison of treatment options 815. Each treatment option (e.g., coil embolization, parent artery occlusion, liquid embolies, and flow diversion) in the comparison 815 may be associated with a therapeutic product or device (e.g., Axium progressive coil, Axium MicroFX PGLA and Nylon microfilaments, Onyx HD-500, and Pipeline flow diversion device) that may be used if the treatment option is selected to treat the patient's medical condition. Links to more detailed information (e.g., case reports) about the use of the therapeutic products or devices with the treatment options may also be provided.

Figure 8C:
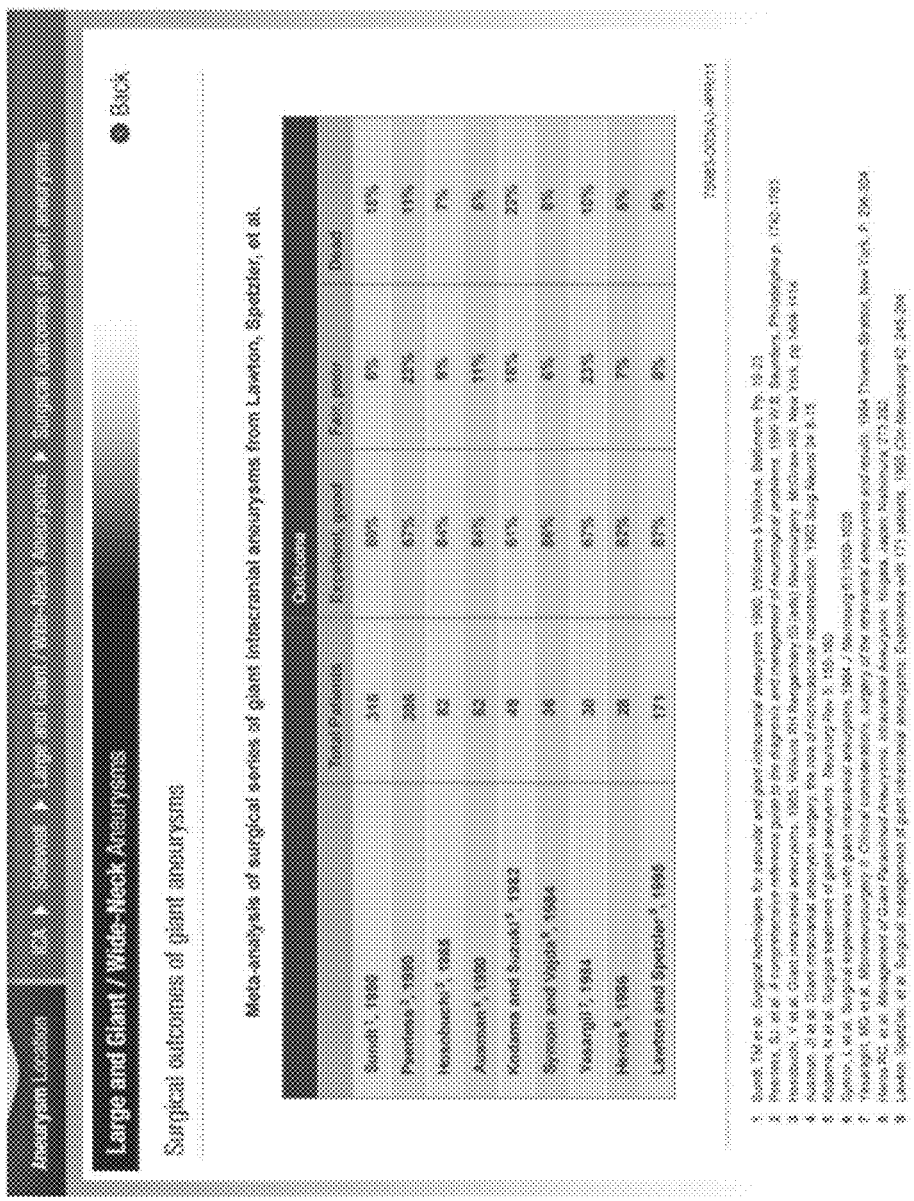
FIG. 8C is a graphical interface that displays items of clinical information, in accordance with some aspects of the subject technology.

FIG. 8C is a graphical interface 880 that displays items of clinical information, in accordance with some aspects of the subject technology. More specifically, FIG. 8C illustrates a graphical interface showing information about surgical outcomes of giant aneurysms that may be reached by the user selecting the natural history link 805 displayed in graphical interface 800 of FIG. 8A. In some aspects, the surgical outcome information may be a summary of one or more studies and include visual aids (e.g., charts, tables, images, graphs, etc.) to help a user digest the information. References may also be provided on the graphical interface 880 in order to allow users to find the studies for further research.

In some aspects, different sets of graphical interfaces and different sets of items of clinical information may be generated for each combination of user selections received from the user. The items of clinical information may include charts, tables, videos, images, audio recordings, or other media that may be used to help a user determine a treatment plan for a patient's medical condition.

Figure 9:
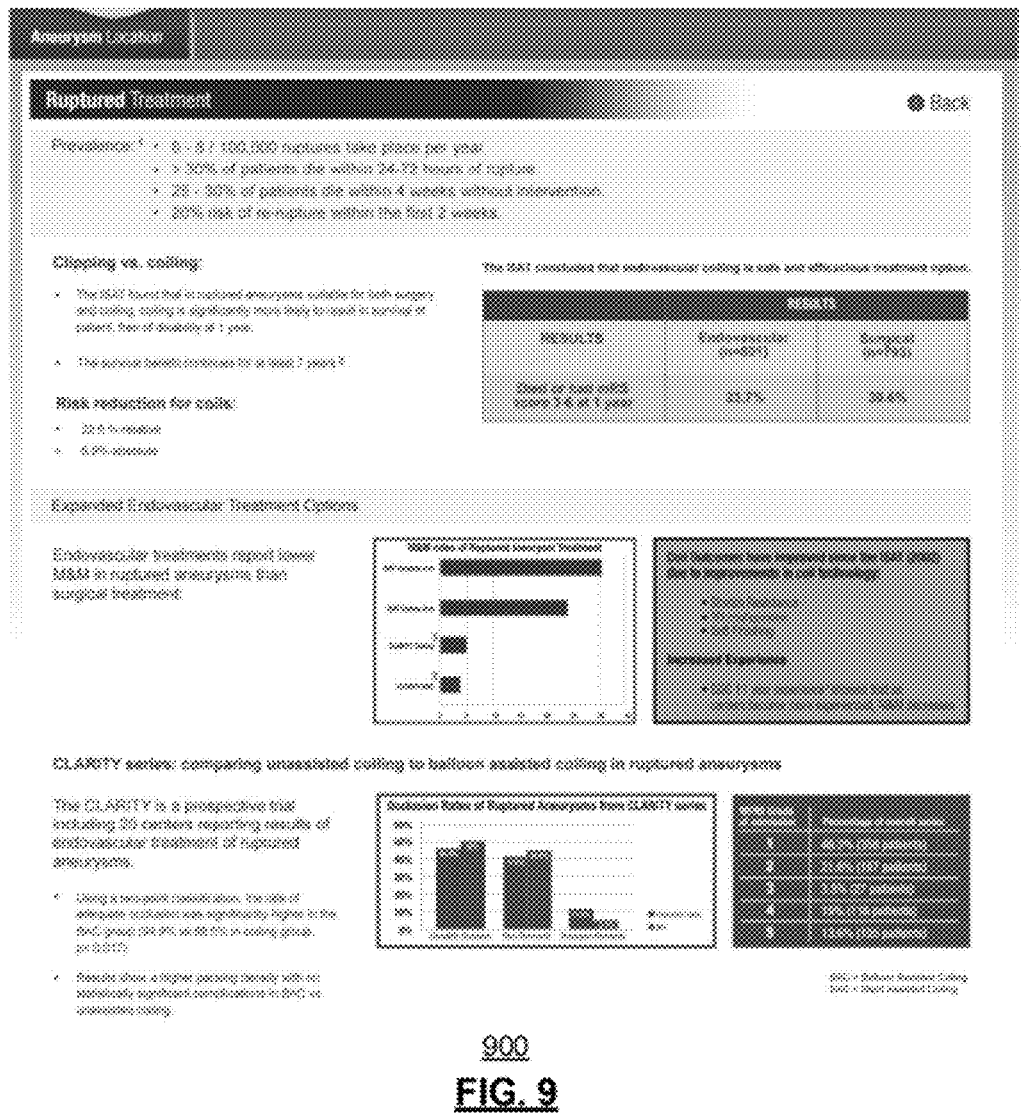
FIG. 9 is a graphical interface that displays items of clinical information, in accordance with some aspects of the subject technology.

FIG. 9 is a graphical interface 900 that displays items of clinical information, in accordance with some aspects of the subject technology. More specifically, FIG. 9 illustrates a graphical interface 900 showing treatment options for ruptured aneurysms that may be reached by the user selecting the ruptured aneurysm treatment link displayed in graphical interfaces 600 of FIG. 6A, 700 of FIG. 7A, and 800 of FIG. 8A. The graphical interface 900 includes information about ruptured aneurysms such as prevalence information, treatment options, comparative results, updates in treatment technology, and particular products that may be used to treat the ruptured aneurysms.

In some aspects of the subject technology, a user may be presented with items of clinical information at any point in the process. In some aspects, instead of determining a second set of morphologies based on the user selection of one of the first set of morphologies as was done at operation 230 in FIG. 2, the system may instead identify one or more items of clinical information and display the items of clinical information to the user on the graphical interface. Further aspects may be illustrated with reference to FIG. 10A and FIG. 10B.

Figure 10A:
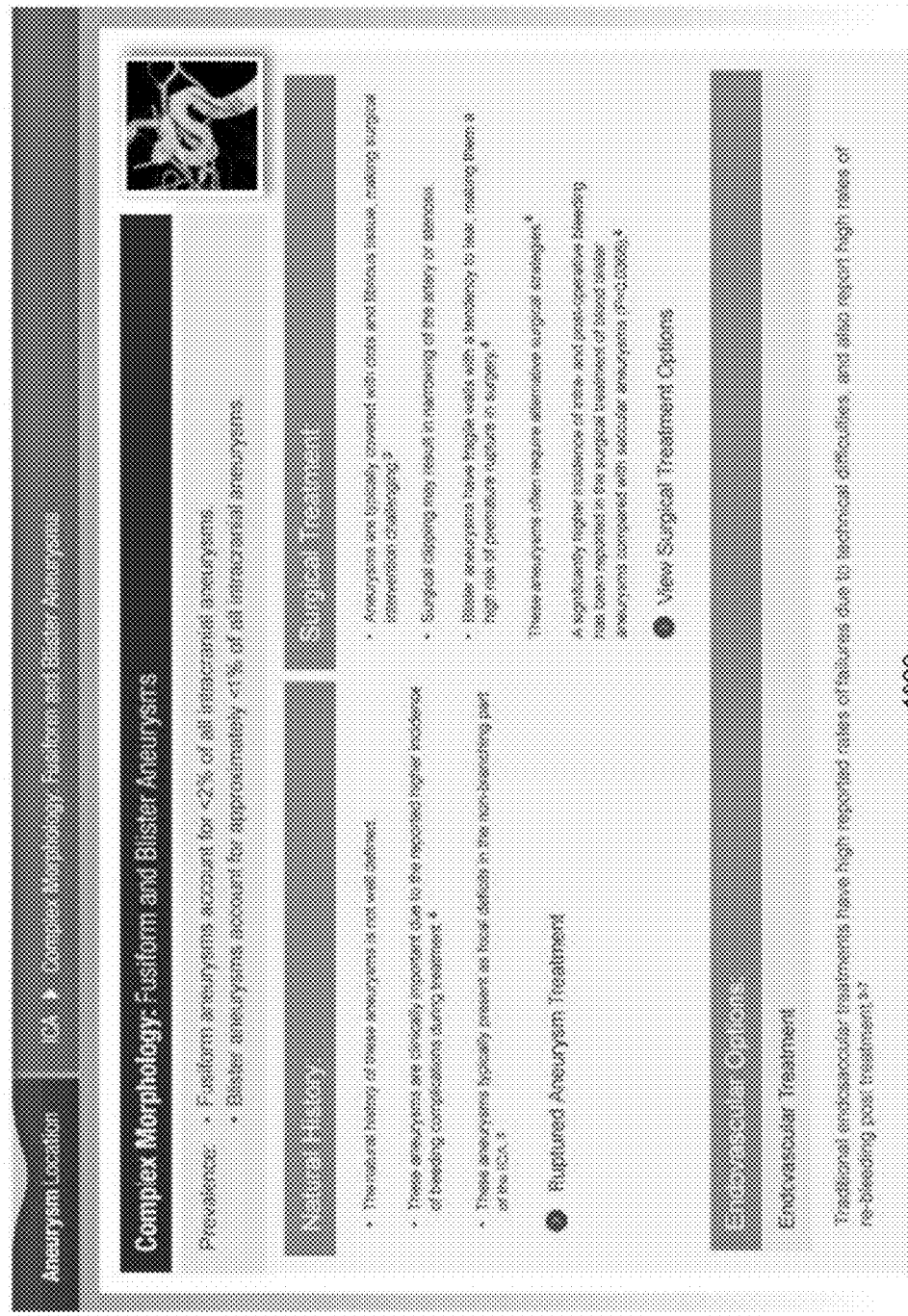
FIG. 10A is a portion of a graphical interface that displays items of clinical information, in accordance with some aspects of the subject technology.

FIG. 10A is a portion of a graphical interface 1000 that displays items of clinical information, in accordance with some aspects of the subject technology. The graphical interface 1000 may be displayed to the user in response to various user selections. For example, graphical interface 1000 may be displayed in response to the user selecting the "Complex Morphology" in the graphical interface 400 in FIG. 4. Graphical interface 1000 displays a number of items of clinical information related to aneurysms with complex morphologies (e.g., fusiform and blister aneurysms) that may be found on the ICA.

Graphical interface 1000 may includes information such as prevalence information, information about the natural history of aneurysms with complex morphologies, information about surgical treatment options, and information about endovascular treatment options. The information may include a summary of research, studies, or trials, information about difficulties with treatment options, statistics, charts, or other visual aids. Links to additional information may also be provided.

Figure 10B:
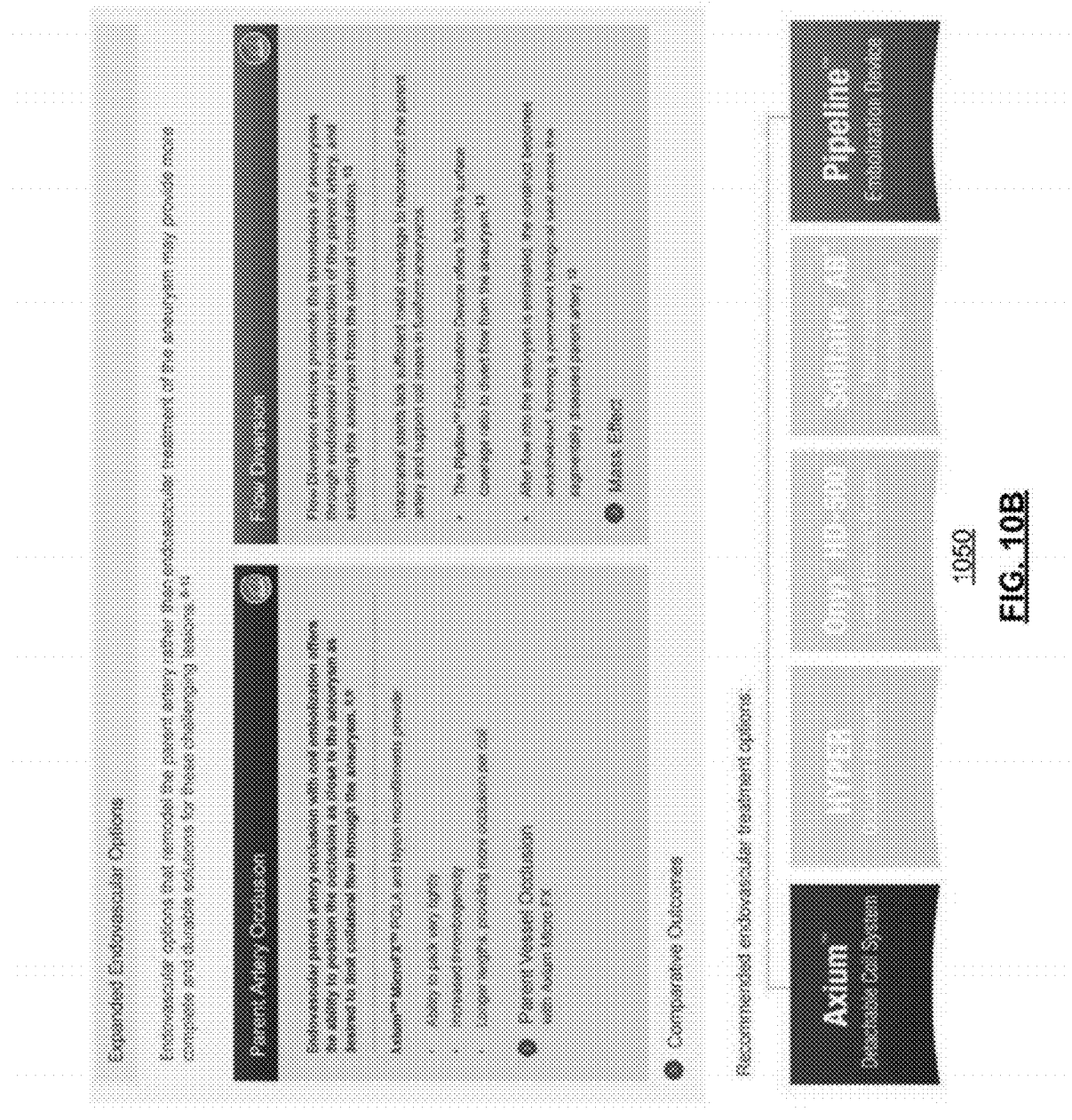
FIG. 10B is a portion of a graphical interface that displays items of clinical information, in accordance with some aspects of the subject technology.

FIG. 10B is a portion of a graphical interface 1050 that displays items of clinical information, in accordance with some aspects of the subject technology. In some aspects, the portion of the graphical interface 1050 may appear right below the portion of the graphical interface 1000 illustrated in FIG. 10A. The bottom portion of the graphical interface 1050 may include information about parent artery occlusion that is associated with a particular device or product (e.g., Axium MicroFX) and information about flow diversion that is also associated with a particular device or product (e.g., Pipeline embolization devices). The graphical interface 1050 may also include recommended treatment options and links to a more information about recommended products associated with the treatment options. The links may lead to additional graphical interfaces with more detailed information on each of the treatment options and associated therapeutic products as well as comparative outcomes.

Figure 11:
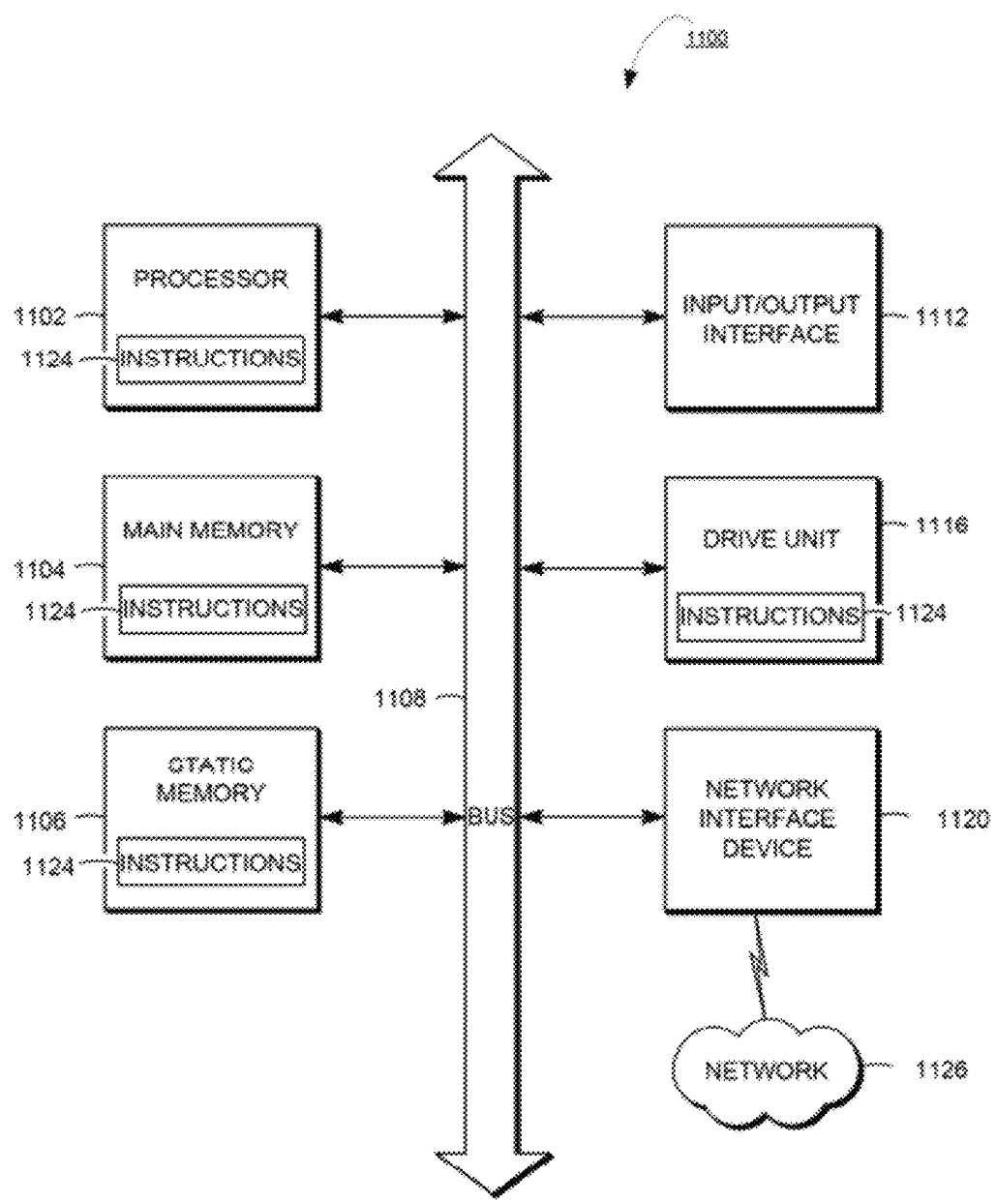
FIG. 11 is a block diagram illustrating a computer system with which any of the clients and servers of FIG. 1 may be implemented.

FIG. 11 is a block diagram illustrating a computer system with which any of the clients and servers of FIG. 1 may be implemented. In certain aspects, the computer system 1100 may be implemented using hardware or a combination of software and hardware, either in a dedicated server, or integrated into another entity, or distributed across multiple entities.

The example computer system 1100 includes a processor 1102, a main memory 1104, a static memory 1106, a disk drive unit 1116, and a network interface device 1120 which communicate with each other via a bus 1108. The computer system 1100 may further include an input/output interface 1112 that may be configured to communicate with various input/output devices such as video display units (e.g., liquid crystal (LCD) displays, cathode ray tubes (CRTs), or touch screens), an alphanumeric input device (e.g., a keyboard), a cursor control device (e.g., a mouse), or a signal generation device (e.g., a speaker).

Processor 1102 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

A machine-readable medium (also referred to as a computer-readable medium) may store one or more sets of instructions 1124 embodying any one or more of the methodologies or functions described herein. The instructions 1124 may also reside, completely or at least partially, within the main memory 1104 and/or within the processor 1102 during execution thereof by the computer system 1100, with the main memory 1104 and the processor 1102 also constituting machine-readable media. The instructions 1124 may further be transmitted or received over a network 1126 via the network interface device 1120.

The machine-readable medium may be a single medium or multiple media (e.g., a centralized or distributed database, and/or associated caches and servers) that store the one or more sets of instructions. The machine-readable medium may include the drive unit 1116, the static memory 1106, the main memory 1104, the processor 1102, an external memory connected to the input/output interface 1112, or some other memory. The term "machine-readable medium" shall also be taken to include any non-transitory medium that is capable of storing, encoding or carrying a set of instructions for execution by the machine and that cause the machine to perform any one or more of the methodologies of the embodiments discussed herein. The term "machine-readable medium" shall accordingly be taken to include, but not be limited to, storage mediums such as solid-state memories, optical media, and magnetic media.

Systems, methods, and machine-readable media for aiding treatment of a vascular disease are described. According to various aspects of the subject technology, a system may be configured to help a user identify the particular set of characteristics of a patient's known medical condition and one or more treatment options that fit those set of characteristics of the patient's medical condition. For example, the system may be used to identify a region of interest that represents a distinct anatomic site in the patient's body where an event or medical condition occurred. Based on where in the patient's body the event or medical condition occurred, the system may present a set of morphologies to the user to enable the user to further characterize the patient's medical event or condition.

After the user specifies a characteristic of the patient's medical event or condition by selecting one morphology out of the set of morphologies, the system may generate further sets of morphologies based on the characteristics already specified by the user in order to further identify characteristics of the patient's medical event or condition and eventually present the user with a number of treatment options directed to the patient's medical diagnoses and information about the treatment options.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts, Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects.

The word "exemplary" may be used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method of aiding interventional treatment of a vascular disease, comprising:
displaying at an interface (i) a graphical representation of at least a portion of a vascular area comprising at least one of an arterial bifurcation and a venous confluence, (ii) a plurality of regions of interest at locations in the representation, each of the regions representing a distinct anatomic site of an event at the vascular area, and (iii) an incident rate of the medical event at each anatomic site;
wherein the event comprises at least one of thrombosis, rupture, and bleeding;
receiving from a user a first selection, of a first of the regions, the first region representing a first site among the plurality of anatomic sites;
determining, using a processor and based on the first selection, a first set of pathological morphologies and at least two diseases of the first site, each member of the first set being clinically associated with occurrence of the event at a diseased portion of the first site;

wherein one of the diseases comprises aneurysms, and another of the diseases comprises arteriovenous malformations;

displaying the members of the first set to the user;

receiving from the user a second selection, of a first member of the first set;

determining, using a processor and based on the second selection, a second set of pathological morphologies of the first site, each member of the second set comprising at least one of a shape and a size of the diseased portion associated with the first member;

displaying the members of the second set to the user;

receiving from the user a third selection, of a first member of the second set;

determining, based on the third selection, an item of clinical information to display to the user, wherein the item of clinical information comprises information about at least two treatment options comprising one or more endovascular treatments and a surgical treatment, other than the one or more endovascular treatments, a comparison between benefits of the at least two treatment options, a comparison between outcome statistics of the at least two treatment options, and prevalence information comprising an incident rate of the first member at the first site;

wherein the one or more endovascular treatments comprise at least one of coil embolization, parent artery occlusion, liquid embolics, or flow diversion;

wherein the information about each treatment option in the at least two treatment options comprises information about a particular therapeutic device, including device features, device benefits, and at least one of case reports associated with the device or a summary of studies associated with the device; and displaying the item of clinical information to the user, wherein the displaying of the item of clinical information comprises simultaneous display of the at least two treatment options, the comparison between the benefits of the at least two treatment options, the comparison between the outcome statistics of the at least two treatment options, and the prevalence information.

2. The method of claim 1, wherein the diseased portion comprises at least one of an aneurysm and an arteriovenous malformation.

3. The method of claim 1, wherein the item of clinical information comprises a selection of at least one therapeutic device type suitable for treating the diseased portion, wherein selection of the at least one therapeutic device type is based on at least one of the first selection and the second selection.

4. The method of claim 1, wherein the item of clinical information includes at least one link to an interface containing information about the particular therapeutic device.

5. The method of claim 1, wherein the at least two treatment options are associated with the first selection and the second selection.

6. The method of claim 1, wherein the item of clinical information comprises a selection of information about the event at the vascular area, wherein selection of the information about the event is based on at least one of the first selection and the second selection.

7. A non-transitory machine-readable medium comprising instructions stored therein, which when executed by a machine, cause the machine to perform operations comprising:

displaying at an interface (i) a graphical representation of a portion of a mammalian body, (ii) a plurality of regions of interest at locations in the representation, each of the regions representing a distinct anatomic site of a potential medical event, and (iii) an incident rate of the medical event at each anatomic site;

receiving from a user a first selection, of a first of the regions, the first region representing a first site among the plurality of anatomic sites;

determining, based on the first selection, a first set of pathological morphologies and at least two diseases of the first site, each member of the first set being clinically associated with occurrence of the event at a diseased portion of the first site;

wherein one of the diseases comprises aneurysms, and another of the diseases comprises arteriovenous malformations;

displaying the members of the first set to the user;

receiving from the user a second selection, of a first member of the first set;

determining, based on the second selection, a second set of pathological morphologies of the first site, each member of the second set comprising at least one of a shape and a size of the diseased portion associated with the first member;

displaying the members of the second set to the user;

receiving from the user a third selection, of a first member of the second set;

determining, based on the third selection, an item of clinical information to display to the user, wherein the item of clinical information comprises information about at least two treatment options comprising one or more endovascular treatments and a surgical treatment, other than the one or more endovascular treatments, a comparison between benefits of the at least two treatment options, a comparison between outcome statistics of the at least two treatment options, and prevalence information comprising an incident rate of the first member at the first site;

wherein the one or more endovascular treatments comprise at least one of coil embolization, parent artery occlusion, liquid embolics, or flow diversion;

wherein the information about each treatment option in the at least two treatment options comprises information about a particular therapeutic device, including device features, device benefits, and at least one of case reports associated with the device or a summary of studies associated with the device; and displaying the item of clinical information to the user, wherein the displaying of the item of clinical information comprises simultaneous display of the at least two treatment options, the comparison between the benefits of the at least two treatment options, the comparison between the outcome statistics of the at least two treatment options, and the prevalence information.

8. The non-transitory machine-readable medium of claim 7, wherein the graphical representation of a portion of the mammalian body comprises a vascular area of the mammalian body.

9. The non-transitory machine-readable medium of claim 7, wherein the diseased portion comprises at least one of an aneurysm and an arteriovenous malformation.

10. The non-transitory machine-readable medium of claim 7, wherein the item of clinical information comprises a selection of at least one therapeutic device type suitable for treating the diseased portion, wherein selection of the at least one therapeutic device type is based on at least one of the first selection and the second selection.

11. The non-transitory machine-readable medium of claim 7, wherein the item of clinical information includes at least one link to an interface containing information about the particular therapeutic device.

12. The non-transitory machine-readable medium of claim 7, wherein the item of clinical information comprises a selection of information about the event, wherein selection of the information about the event is based on at least one of the first selection and the second selection.

13. A system of aiding interventional treatment of a vascular disease, the system comprising:
an output interface configured to present data;
an input interface configured to receive input data;
a processor; and
a storage device configured to store instructions that, when executed by the processor, cause the processor to:
display, at the output interface, (i) a graphical representation of at least a portion of a vascular area comprising at least one of an arterial bifurcation and a venous confluence, (ii) a plurality of regions of interest at locations in the representation, each of the regions representing a distinct anatomic site of an event at the vascular area, and (iii) an incident rate of the medical event at each anatomic site;
wherein the event comprises at least one of thrombosis, rupture, and bleeding;
receive, via the input interface, a first selection, of a first of the regions, the first region representing a first site among the plurality of anatomic sites;
determine, based on the first selection, a first set of pathological morphologies and at least two diseases of the first site, each member of the first set being clinically associated with occurrence of the event at a diseased portion of the first site;
wherein one of the diseases comprises aneurysms, and another of the diseases comprises arteriovenous malformations;
display, at the output interface, the members of the first set to the user;
receive, via the input interface, a second selection, of a first member of the first set;
determine, based on the second selection, a second set of pathological morphologies of the first site, each member of the second set comprising at least one of a shape and a size of the diseased portion associated with the first member;
display, at the output interface, the members of the second set to the user;
receive, via the input interface, a third selection, of a first member of the second set;
determine, based on the third selection, an item of clinical information to display to the user, wherein the item of clinical information comprises information about at least two treatment options comprising one or more endovascular treatments and a surgical treatment, other than the one or more endovascular treatments, a comparison between benefits of the at least two treatment options, a comparison between outcome statistics of the at least two treatment options, and prevalence information comprising an incident rate of the first member at the first site;
wherein the one or more endovascular treatments comprise at least one of coil embolization, parent artery occlusion, liquid embolics, or flow diversion;
wherein the information about each treatment option in the at least two treatment options comprises information about a particular therapeutic device, including device features, device benefits, and at least one of case reports associated with the device or a summary of studies associated with the device; and
display, at the output interface, the item of clinical information to the user, wherein the displaying of the item of clinical information comprises simultaneous display of the at least two treatment options, the comparison between the benefits of the at least two treatment options, and the comparison between the outcome statistics of the at least two treatment options, and the prevalence information.

* * * * *